United States Patent
Cochran et al.

(10) Patent No.: US 6,710,194 B1
(45) Date of Patent: Mar. 23, 2004

(54) EPOXIDATION PROCESS

(75) Inventors: Robert N. Cochran, West Chester, PA (US); Prakash G. Balan, Wilmington, DE (US); Mark A. Liepa, Exton, PA (US); Bernard Cooker, Malvern, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/349,655

(22) Filed: Jan. 23, 2003

(51) Int. Cl.[7] ............................................. C07D 301/06
(52) U.S. Cl. ......................................... 549/533; 549/532
(58) Field of Search .................................. 549/533, 532

(56) References Cited

U.S. PATENT DOCUMENTS

| | | | | |
|---|---|---|---|---|
| 5,744,619 A | * | 4/1998 | Nemeth et al. | 549/523 |
| 5,780,654 A | * | 7/1998 | Nemeth et al. | 549/531 |
| 6,005,123 A | * | 12/1999 | Dessau et al. | 549/539 |
| 6,008,388 A | * | 12/1999 | Dessau et al. | 549/531 |
| 6,281,369 B1 | * | 8/2001 | Cooker et al. | 549/533 |

* cited by examiner

Primary Examiner—Ba K. Trinh
(74) Attorney, Agent, or Firm—William C. Long

(57) ABSTRACT

Propylene oxide is produced by liquid phase reaction of propylene oxygen and hydrogen in contact with a solid epoxidation catalyst at elevated temperature and pressure, the reaction conditions being regulated to provide a weight ratio of dissolved oxygen to dissolved hydrogen in the liquid reaction mixture of at least 16.

10 Claims, 2 Drawing Sheets

EPOXIDATION PROCESS

FIELD OF THE INVENTION

This invention relates to the epoxidation of olefins such as propylene by reaction of the olefin with hydrogen and oxygen using a noble metal on titanium or vanadium silicalite catalyst, an essential feature of the invention being that reaction conditions are maintained so that both high rate and high selectivity is achieved.

BACKGROUND OF THE INVENTION

Epoxides constitute an important class of chemical intermediates useful for the preparation of polyether polyols, glycols, glycol ethers, surfactants, functional fluids, fuel additives and the like. Many different methods for synthesizing epoxides from the corresponding olefins have been described in the literature. A Japanese patent application assigned to the Tosoh Corporation and published in 1992 (Kokai No. 4-352771) proposed making propylene oxide by reacting propylene, hydrogen and oxygen using a catalyst comprising a Group VIII metal and a crystalline titanosilicate. U.S. Pat. Nos. 6,281,369, 6,005,123 and 6,008,388 are also relevant. As with any chemical process, it would be desirable to attain further improvements in epoxidation methods of this type and it is to such improvements that this invention is directed.

SUMMARY OF THE INVENTION

There are several important process features which must be carefully regulated in order to achieve the benefits of the present invention. Chief among these is conducting the reaction so as to maintain high hydrogen conversion while at the same time maintaining very low concentrations of hydrogen in the reacting gases. At the same time, moderate oxygen conversion and high oxygen to hydrogen partial pressure ratios are maintained. The reaction is a continuous one and is carried out in a fully back mixed CSTR or in a packed bed plug flow reactor with a high recirculation ratio.

DESCRIPTION OF THE DRAWINGS

The accompanying FIG. 1 illustrates practice of the invention using a CSTR reactor while

DETAILED DESCRIPTION

Figure 1:
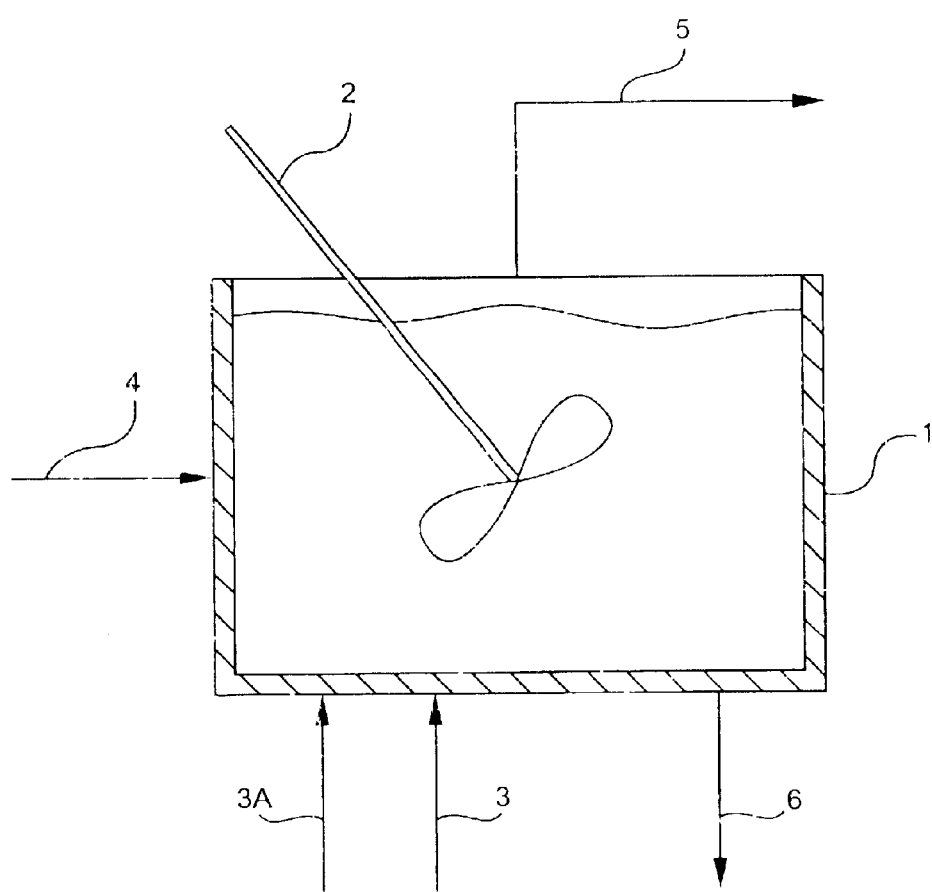

The epoxidation reaction according to the present invention is a continuous reaction wherein hydrogen, oxygen and propylene are fed to a suitable reaction zone and product propylene oxide is continuously removed therefrom. Essential to achieving the advantages of this invention is the provision of a fully back-mixed reaction zone containing a slurry of solid catalyst in a suitable liquid reaction medium with sufficient agitation to insure completely back-mixed conditions, or the provision of a fixed bed plug flow reactor with very high vapor recirculation rates or multiple hydrogen injection points.

In general, catalysts, solvents and reagents are employed which are known for this reaction. Thus, hydrogen, oxygen and propylene are the essential reactants. A ballast gas is conveniently used. Propane, propylene and mixtures are illustrative.

The epoxidation is carried out in the liquid phase. Advantageously a solvent is used, preferred solvents being methanol or water or methanol/water mixtures. The dense phase procedure using carbon dioxide solvent described in copending application Ser. No. 09/981,198 filed Oct. 16, 2001, can be used. The disclosure of said Ser. No. 09/981,198 is incorporated herein by reference.

The catalysts to be used in the present invention are composed of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The choice of zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite or vanadium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1"(having an MEL topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures, isomorphous to zeolite beta, mordenite, ZSM-48, ZSM-12 and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium as described in U.S. Pat. Nos. 5,780,654 and 5,744,619.

Preferred titanium-containing zeolite catalysts suitable for use in the process of this invention will generally have a composition corresponding to the following empirical formula: $xTiO_2(1-x)SiO_2$, where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites. may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent. Suitable catalysts are described in U.S. Pat. Nos. 6,281,369, 6,005,123 and 6,008,388 the disclosure of which are incorporated herein by reference.

The amount of catalyst used may be determined on the basis of the molar ratio of the titanium contained in the titanium zeolite to the olefin that is supplied per unit of time. Typically, sufficient catalyst is present to provide a feed ratio of from about 10 to 100,000 lbs of propylene/hr per lb of titanium.

The epoxidation is carried out in the liquid phase, and it is advantageous to work at elevated pressure of 1–100 bars gauge. Suitable solvents used in catalyst preparation and in the epoxidation include, but are not limited to, lower aliphatic alcohols such as methanol, ethanol, isopropanol, and tert-butanol, or 35 mixtures thereof, and water. Fluorinated alcohols can be used. It is also possible to use mixtures of the cited alcohols with water. Methanol and methanol/water are preferred. Supercritical carbon dioxide solvent can also be used. Additional solvent can be added before or during epoxidation to improve process results.

Epoxidation according to the invention is carried out at a temperature effective to achieve the desired propylene epoxidation, preferably at temperatures in the range of 0–125° C., more preferably 20–80° C. The reaction is carried out at elevated pressures not to exceed about 100 bars gauge, preferably in the range 2–80 bars gauge.

As the carrier gas, inert gases such as helium, neon, argon, krypton and xenon are suitable as well as nitrogen and carbon dioxide. Saturated hydrocarbons with 1–8, especially 1–6, and preferably with 1–4 carbon atoms, e.g., methane, ethane, propane and n-butane, are also suitable. Nitrogen and saturated $C_1$–$C_4$ hydrocarbons are the preferred carrier gases. Mixtures of the listed carrier gases can also be used.

In carrying out the process of the invention, it is essential that the weight ratio of oxygen to hydrogen dissolved in the reaction mixture be at least 16 part by weight oxygen per part by weight hydrogen. Weight ratios of dissolved oxygen to dissolved hydrogen of at least 32 are preferred, and ratios of at least 50 are more preferred.

Additionally, it is important that the concentration of hydrogen dissolved in the liquid reaction mixture not exceed about 19 ppmw; concentrations of hydrogen dissolved in the liquid reaction mixture preferably are in the range 0.1 to 10 ppmw. Liquid phase dissolved oxygen concentrations should not exceed 1390 ppmw.

In establishing appropriate reaction conditions, it is necessary to set the exit gas oxygen concentration below the flammability limit, preferably at less than about 15 vol. %, more preferably at less than about 10 vol. %.

Referring to the attached FIG. 1, reactor 1 is a continuously stirred tank reactor (CSTR) containing a slurry of solid catalyst particles in the reaction liquid. Agitator 2 provides continuous agitation to the mixture.

Reactants comprised of hydrogen, and propylene are continuously introduced via line 3 to the reactor together with ballast gas if used. Oxygen is separately introduced via line 3A, the purpose of the separate introduction being to avoid formation of flammable mixtures. A liquid stream comprised of solvent together with slurried catalyst particles is introduced to the reactor via line 4. Sufficient rates of agitation are maintained in reactor 1 such that the composition of the reaction mixture therein is substantially the same throughout the reactor, i.e. there is less than about 20% variation in composition in the reaction liquid. A vapor stream comprised of unreacted oxygen, such hydrogen as is unreacted, water, solvent, propylene, and the like is continuously removed via line 5 and the liquid reaction mixture slurry containing product epoxide is continuously removed via line 6.

In order to insure proper functioning of the system it is important to provide sufficient hydrogen in the gases fed to the system via line 3. In order to achieve sufficient hydrogen input while also maintaining very low hydrogen concentration in the reaction mixture it is essential that complete back mixing of the reaction mixture slurry be maintained and that the concentration by volume of hydrogen in the exit gases is low. Also, it is essential that the slurry/gas mixture be very well agitated, to obtain sufficient gas to liquid mass transfer of the hydrogen, given the low hydrogen concentration deriving force.

A further important consideration is the provision or high oxygen to hydrogen ratios in the reaction liquid as above described. The maximum oxygen concentration is governed by the flammable oxygen composition, i.e. the oxygen concentration in the reaction vapor must be maintained below the level at which flammable or explosive mixtures are formed in order to avoid explosion hazards during operation. Oxygen in excess of that needed for complete reaction is fed via line 3A, preferably the maximum amount below that at which flammable mixtures are formed. The system is maintained such that the concentration by volume of oxygen in the exit gases is lower than the flammable limit, preferably lower than 15 vol. %, more preferably lower than 10 vol. %.

The system is regulated to give as high a volume ratio of $O_2/H_2$ as possible in the exit gases. Preferably, this ratio is at least 2/1.

The reaction mixture composition should be as uniform as possible throughout the entire reaction zone. It is important that reactor mixing be adequate to prevent the weight ratio of dissolved oxygen to dissolved hydrogen from dropping below 16/1 in any portion of the liquid reaction mixture. In order to achieve high reaction rates and selectivites, the composition of the liquid reaction mixture components should be uniform throughout the entire reaction mixture.

The standard deviation of the composition should be within plus or minus about 20% of the average reaction mixture composition. In the case of a CSTR this requires a high rate of agitation of the reaction mixture slurry, i.e. an agitation rate of at least 5 hp/1000 gal or the equivalent, preferably at least 10 hp/1000 gal. In the case of a fixed bed plug flow reactor, the vapor components of the reaction mixture are recycled at a high rate, e.g at least 1 volume of recycle per volume of net feed, preferably at least 2 volumes of recycle per volume of net feed. Alternatively or in combination with vapor recycle, appropriate recycle of a portion of the reaction liquid can be provided.

Figure 2:
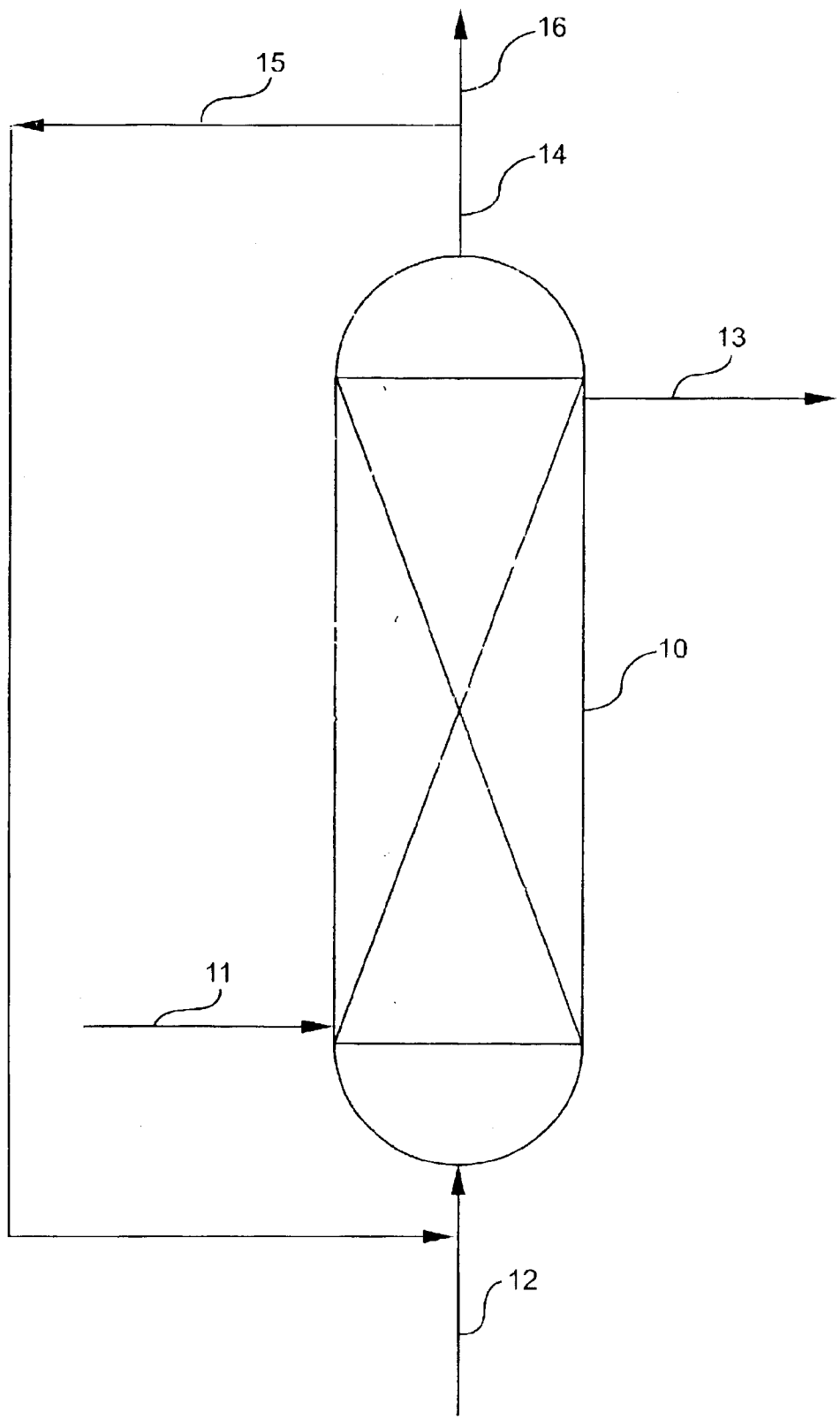
FIG. 2 illustrates plug flow practice.

FIG. 2 illustrates practice of the invention wherein a fixed bed, plug flow reactor is employed. Referring to FIG. 2, reactor 10 is a conventional fixed bed reactor packed with a suitable solid epoxidation catalyst.

A liquid solvent stream, illustratively methanol is introduced via line 11. A vapor feed stream comprised of propylene, hydrogen and oxygen together with ballast gas is passed via line 12 and combined with a vapor recycle stream via line 15 and the combined stream is introduced into reactor 10 wherein suitable reaction conditions are maintained and propylene oxide product is formed.

Liquid reaction product mixture is removed from reactor 10 via line 13 and passes to product work up and recovery.

A vapor stream is removed from reactor 10 via line 14 and a portion of the vapor stream is recycled via line 15 as shown. A portion of the removed vapor stream passes via line 16 to further treatment (not shown) to recover the values contained therein.

As essential feature of this emoodiment of the invention, a minimum of 50% of the vapors removed via line 14 are recycled via line 15 to reactor 10, preferably at least 80% of the vapors are recycled. This recycle rate is necessary to achieve substantial uniformity throughout the entirety of reactor 10 thus approximating fully back mixed plug flow operation.

As an alternative to high vapor recycle, in an embodiment not illustrated in FIG. 2, hydrogen can be introduced via a series of introduction points along the reactor to provide low hydrogen concentrations at any point.

The invention can, perhaps, best be further described by reference to the following examples.

EXAMPLE 1

In this example, practice of the invention is as described in FIG. 1. The catalyst used is palladium promoted titanium silicalite comprised of about 0.4 wt % palladium on TS-1. Catalyst particle size is about 50 microns. A slurry of the catalyst in methanol comprised by weight 10% catalyst is fed to reactor 1 via line 4 at the rate of 93,000 lbs/hr. Reactor 1 has a slurry volume of about 29,800 gals, residence time for the reaction liquid is about 2 hours.

A vapor mixture comprised by volume of 20% propylene, 20% $H_2$, and 60% ballast gas is fed via line 3 at the rate of 1815 lb-mols/hr. Oxygen is fed via line 3A at the rate of 310 lb-mols/hr.

Reaction conditions in reactor 1 are a temperature of 60° C., pressure of 12.8 bar gauge, and an agitator speed to provide 10 hp/1000 gal. Appropriate concentrations of oxygen and hydrogen in the liquid reaction mixture are achieved by regulation of the concentrations of oxygen and hydrogen in the vapor which is in contact with the reaction liquid considering the temperature and pressure at which the reaction is carried out. Generally equilibrium conditions are assumed. Vapor compositions are readily regulated by appropriate adjustment of feed gas composition and rates.

A liquid reaction mixture is removed via line 6 at the rate of 109,000 lbs/hr. This mixture is comprised by weight of 7.7% catalyst, 77.6% methanol, 9.2% propylene oxide, and 5.5% water plus others. The dissolved hydrogen concentration in the reaction mixture during the reaction is about 0.9 ppmw, oxygen is about 100 ppmw, the $O_2/H_2$ weight ratio is about 111. Variation in composition throughout the reactor liquid does not exceed about 20%. Based on propylene converted, selectivity to propylene oxide is 90%, and based on $O_2$ converted, selectivity to propylene oxide is 71.4%.

A vapor mixture is removed via line 5 at the rate of 1365 lb-mols/hr; this mixture is comprised by mols of 12.5% propylene, 5.0% oxygen, 1.3% hydrogen, 1.4% propane, and 79.8% ballast gas plus others. The volume ratio of oxygen to hydrogen is about 3.8.

In order to not have a flammable feed ($O_2$ on the mixed feed would be 14.6%) the $O_2$ stream is injected separately via line 3A. All the other gas feeds, $H_2$, propylene, ballast gas (propane), are introduced into reactor 1 together through line 3.

We claim:

1. In a process for the production of propylene oxide by reaction of propylene, oxygen and hydrogen in the liquid phase reaction mixture over a solid catalyst at reaction conditions, the improvement comprising maintaining a weight ratio of dissolved oxygen to dissolved hydrogen in the liquid reaction mixture of at least 16.

2. The process of claim 1 wherein the concentration of hydrogen dissolved in the reaction mixture is not greater than 19 ppmw.

3. The process of claim 1 wherein the concentration of oxygen dissolved in the liquid phase is not greater than 1390 ppmw.

4. The process of claim 1 wherein the weight ratio of dissolved oxygen to dissolved hydrogen in the liquid mixture is at least 32.

5. The process of claim 1 wherein the weight ratio of dissolved oxygen to dissolved hydrogen in the liquid mixture is at least 50.

6. The process of claim 1 wherein the reaction is carried out in a fully back mixed continuously stirred tank reaction system with an agitation rate equivalent to at least 5 hp/1000 gal.

7. The process of claim 1 wherein the reaction is carried out in a plug flow fixed bed reaction system wherein at least 50% of vapors exiting the reaction system are recycled.

8. The process of claim 1 wherein an exit gas stream is continuously removed from the reaction system comprised of oxygen and hydrogen, the oxygen concentration in said exit gas stream being less than 15 volume % and the volumetric of oxygen to hydrogen in said exit gas stream being at least 2/1.

9. The process of claim 4 wherein the oxygen concentration in said exit gas stream is less than 10 vol. % and the volumetric ratio of oxygen to hydrogen is at least 3/1.

10. The process of claim 1 wherein the reaction pressure is not greater than 100 bars gauge.

\* \* \* \* \*